United States Patent
Sako et al.

(10) Patent No.: US 11,154,469 B2
(45) Date of Patent: Oct. 26, 2021

(54) FLUORESCENT MATERIAL FOR COSMETICS, AND COSMETIC

(71) Applicant: SAKAI CHEMICAL INDUSTRY CO., LTD., Sakai (JP)

(72) Inventors: Emi Sako, Sakai (JP); Ryota Ezoe, Sakai (JP); Nanae Ogata, Sakai (JP); Kenji Mori, Sakai (JP)

(73) Assignee: SAKAI CHEMICAL INDUSTRY CO., LTD., Sakai (JP)

( * ) Notice: Subject to any disclaimer, the term of this patent is extended or adjusted under 35 U.S.C. 154(b) by 225 days.

(21) Appl. No.: 16/472,038

(22) PCT Filed: Dec. 19, 2017

(86) PCT No.: PCT/JP2017/045586
§ 371 (c)(1),
(2) Date: Jun. 20, 2019

(87) PCT Pub. No.: WO2018/117117
PCT Pub. Date: Jun. 28, 2018

(65) Prior Publication Data
US 2020/0113793 A1    Apr. 16, 2020

(30) Foreign Application Priority Data
Dec. 20, 2016  (JP) .............. JP2016-246607

(51) Int. Cl.
*A61K 8/24* (2006.01)
*A61Q 1/02* (2006.01)
(52) U.S. Cl.
CPC ............ *A61K 8/24* (2013.01); *A61Q 1/02* (2013.01); *A61K 2800/412* (2013.01); *A61K 2800/434* (2013.01)
(58) Field of Classification Search
CPC . A61K 8/24; A61K 8/02; A61K 8/016; A61K 8/022; A61K 8/0229; A61K 8/025; A61K 8/03; A61K 8/19; A61K 8/55
See application file for complete search history.

(56) References Cited

U.S. PATENT DOCUMENTS

2008/0226566 A1* 9/2008 Poth .................. A61K 33/06
424/52

FOREIGN PATENT DOCUMENTS

| JP | H03-284613 | 12/1991 |
| JP | 6-117127 A | 5/1993 |
| JP | 2005-206613 A | 8/2005 |
| JP | 2015-54950 A | 3/2015 |
| JP | 2016-141780 A | 8/2016 |
| JP | 2016-141781 A | 8/2016 |
| WO | 2016/063847 A1 | 4/2016 |
| WO | 2019/106920 | 6/2019 |

OTHER PUBLICATIONS

Ziao et al (High efficient blue emission of Ce3+ activated Ca4P2O9 for white LEDs, Optical Society of America, vol. 21, No. 25, 2013). (Year: 2013).*
International Search Report and Written Opinion, International Patent Application No. PCT/JP2017/045586, dated Apr. 3, 2018, with English translation of Search Report (9 pages).
Zhao et al., "High efficient blue emission of Ce3+ activated Ca4P2O9 phosphor for white LEDs", Optics Express, Dec. 13, 2013, vol. 21, No. 25, p. 31660-31667.
Ono, Kazuhisa, "Development on light emitting powder and application to cosmetics", Fragrance Journal, pp. 11-16, English abstract, Feb. 1994.
Jia et al., "Single-phased white-light-emitting Ca4(PO4)2O: Ce3+,Eu2+ phosphors based on energy transfer", Dalton Trans., 2015, 44, p. 11399-11407 (2015).

* cited by examiner

*Primary Examiner* — Micah Paul Young
(74) *Attorney, Agent, or Firm* — Hamre, Schumann, Mueller & Larson, P.C.

(57) ABSTRACT

To obtain an inorganic blue fluorescent material that is composed of elements for which there are no suspected harmful effects on humans, and that has excellent texture when applied to skin.
A fluorescent material for a cosmetic being a composite oxide containing from 0.0005 to 0.05 (in terms of a mole ratio relative to 1 mol of phosphorous in a molecule) of Ce in a compound represented by general formula $Ca_aP_bO_c$ ($3.2 \leq a \leq 5.0$, $b=2$, $c=a+5$) and having an average particle diameter of from 1 to 10 μm.

3 Claims, 4 Drawing Sheets

FLUORESCENT MATERIAL FOR COSMETICS, AND COSMETIC

TECHNICAL FIELD

The present invention relates to a calcium phosphate composite oxide, which is a fluorescent material for cosmetics, and a cosmetic containing the same.

BACKGROUND ART

Use of fluorescent material into cosmetic formulation has been publicly known, and cosmetic characteristics with a unique color tone which is not conventional are expected by the color development caused by the fluorescent material. In particular, blue light (approximately 450 nm) is a wavelength that is the most intensely reflected by a person having a beautiful skin, and a compound containing a blue fluorescence is expected to achieve the effect of imparting translucency to skin and achieving beautiful appearance when such a compound containing a blue fluorescence is blended in cosmetic materials. However, known proposed blue fluorescent materials were considered to cause adverse effects on human body, exhibited insufficient color development, and not suitable for mass production. Practically used fluorescent materials are mainly organic fluorescent materials represented by coumarin derivatives and the like. However, there is a concern about stability of such a compound over time, and thus replacement of such a compound with an inorganic material is desired.

Patent Document 1 describes blending of a fluorescent material originated from natural minerals in cosmetics. However, since this uses natural minerals, there are disadvantages such that it is difficult to obtain powder having a stable quality, the safety is not ensured, and, furthermore, the cost is high.

On the other hand, most of the blue fluorescent materials researched for use in displays, WLEDs (white LEDs), and the like utilizes Eu as the light emission center. However, the safety of Eu to the human body is not proved.

Although $Ca_4(PO_4)_2O:Ce^{3+}$ is a publicly known substance (Patent Document 2, Non-patent Documents 1 and 2, and the like), it has been researched only for the use in WLEDs, and there is no research for blending it into cosmetics. That is, researches have been mainly conducted on particles grown large to increase emission intensities. A fluorescent material in which a particle has been grown is not suitable for blending in cosmetics due to its poor texture. Therefore, powder that is suitable for blending in cosmetics has not been known.

The inventors of the present invention disclosed blue fluorescent materials in which a silica particle contains cerium; and phosphorus and/or magnesium in Patent Documents 3 and 4. However, the compound described therein was a compound utilizing a silica particle as a base substance and was not a compound utilizing calcium phosphate as a base substance.

CITATION LIST

Patent Literature

Patent Document 1: JP 2005-206613 A
Patent Document 2: JP 2015-054950 A
Patent Document 3: JP 2016-141781 A
Patent Document 4: JP 2016-141780 A

Non-Patent Literature

Non-patent Document 1: "Single-phased white-light-emitting $Ca_4(PO_4)_2O:Ce^{3+},Eu^{2+}$ phosphors based on energy transfer" Dalton Trans., 2015, 44 11399-11407
Non-patent Document 2: "High efficient blue emission of $Ce^{3+}$ activated $Ca_4P_2O_9$ phosphor for white LEDs" OPTICS EXPRESS Vol. 21, No. 25 (16, December 2013) 31660-31667

SUMMARY OF INVENTION

Technical Problem

The inventors of the present invention conducted a study on a fluorescent material that is safe and achieves excellent color development, and the study was performed to obtain an inorganic blue fluorescent material that is composed of elements from which no harmful effects on human bodies are suspected and that has excellent texture when applied to skin.

Solution to Problem

An embodiment of the present invention is a fluorescent material for cosmetics, the fluorescent material being a composite oxide containing from 0.0005 to 0.05 (in terms of a mole ratio relative to 1 mol of phosphorous in a molecule) of Ce in a compound represented by general formula $Ca_aP_bO_c$ ($3.2 \leq a \leq 5.0$, $b=2$, $c=a+5$) and having an average particle diameter of from 1 to 10 μm.

The fluorescent material for cosmetics described above preferably further contains from 20 to 10000 ppm of potassium relative to the weight of the fluorescent material for cosmetics.

Another embodiment of the present invention is a cosmetic containing the fluorescent material for cosmetics described above.

Advantageous Effects of Invention

The fluorescent material for cosmetics of an embodiment of the present invention achieves excellent effects, such as excellent color development, high safety, and excellent texture when blended into cosmetics and applied on skin.

DESCRIPTION OF EMBODIMENTS

An embodiment of the present invention is a fluorescent material for cosmetics, the fluorescent material being a composite oxide containing from 0.0005 to 0.05 (in terms of a mole ratio relative to 1 mol of phosphorous in a molecule) of Ce in a compound represented by general formula $Ca_aP_bO_c$ ($3.2 \leq a \leq 5.0$, $b=2$, $c=a+5$) and having an average particle diameter of from 1 to 10 µm.

That is, the fluorescent material has a chemical structure in which calcium phosphate is doped with a cerium element. The compound having such a structure is a powder having blue fluorescence and can be obtained by using no element that gives adverse effect on human bodies. This is a preferable material from the perspective of the light emission characteristics, by which light emission occurs in a wide wavelength range, thus being natural and easily visually observable.

Furthermore, although such a fluorescent material is a publicly known compound, the fluorescent material has been researched and developed for use in WLEDs, and thus the most important research objective thereof has been the enhancement of light emission performances. Therefore, no study has been conducted for an aspect, preferable for use in cosmetics, of the compound described above. That is, a particle that can achieve excellent texture when used as cosmetics has not been known. The inventors of the present invention found that the fluorescent material having the composition described above and having an average particle diameter of from 1 to 10 µm achieves excellent performance as a cosmetic raw material and thus completed the present invention.

In the composition formula described above, calcium phosphate is partially doped with cerium; however, the composition formula may be slightly off the chemical equivalent, and thus from such perspective, the composition formula may be in the range of $3.2 \leq a \leq 5.0$ or preferably $3.6 \leq a \leq 4.7$. Furthermore, the range may be preferably $4.0 < a$, with which calcium is slightly excessive. The fluorescent material having excessive amount of calcium is preferable from the perspective of achieving excellent light emission characteristics. Furthermore, excessive amount of calcium leads to the prevention of excessive sintering and ease in cracking and thus is preferable and advantageous when the average particle diameter is controlled to be within the range of the present invention, which is from 1 to 10 µm.

Furthermore, for known fluorescent materials described in Patent Document 2 and the like, a part of calcium is replaced with Sr or Ba. This is because the light emission characteristics change, or the light emission intensity is increased by the combined use of Sr or Ba. However, in the present application, the content of Sr and Ba is preferably reduced. This is because it is conceived that Sr and Ba are not preferable from the perspective that these elements are not proved to be safe in cosmetics. More specifically, the total amount of Sr and Ba is preferably 500 ppm or less relative to the weight of the fluorescent material for cosmetics.

Furthermore, the content of Ce is in the range of 0.0005 to 0.05 (mole ratio relative to 1 mol of phosphorus in a molecule). Excellent light emission performance can be achieved by this range. The lower limit of the content of Ce described above is more preferably 0.0015 and even more preferably 0.0025. The upper limit of the content of Ce described above is more preferably 0.035 and even more preferably 0.025.

The study conducted by the inventors of the present invention also revealed that the content of Ce described above affects the dominant wavelength of the light emission. That is, as the content of Ce increases, the dominant wavelength shifts toward a longer wavelength side. By utilizing this, it is also possible to adjust the color tone of the fluorescent material for cosmetics of an embodiment of the present invention.

The maximum emission wavelength (also referred to as "dominant wavelength") of the emission spectrum of the fluorescent material for cosmetics described above at the time when the excitation light having the wavelength of 365 nm is irradiated is preferably from 420 nm to 480 nm. The dominant wavelength of 420 nm or greater is preferable from the perspective of reducing the proportion of ultraviolet light contained in the light emission. Such a dominant wavelength is varied by adjustment of the composition and/or additives described below, and by adjusting these factors, it is possible to set the dominant wavelength from 420 nm to 480 nm. The dominant wavelength described above is more preferably from 430 nm to 475 nm and even more preferably from 440 nm to 470 nm. Note that the dominant wavelength in the present specification is a value measured by the method described in Examples.

Furthermore, the fluorescent material for cosmetics of an embodiment of the present invention may be a fluorescent material that emits light by excitation light that is in the visible light region. The "fluorescent material that emits light by excitation light that is in the visible light region" is a fluorescent material that emits light having the dominant wavelength of the emission spectrum in the range of 485 nm to 510 nm when the excitation light having the wavelength of 405 nm is irradiated.

The fluorescent material that emits light by excitation light that is in the visible light region described above is a fluorescent material that emits fluorescence in response to indoor light composed mainly of visible light without ultraviolet light because the fluorescent material emits fluorescence by excitation light in the visible light region. Therefore, the fluorescent material can be used as a cosmetic raw material that emits light outdoor and indoor.

The fluorescent material for cosmetics described above may contain other elements in the range that does not affect safety on human bodies and performances. Examples of such other elements include alkali metal elements, such as Li, Na, and K; alkaline earth metal elements, such as Be and Ra; other metal elements, such as Y, Zr, V, Nb, Cr, Mo, W, Fe, Co, Ni, Pd, Pt, Cu, Ag, Zn, B, Al, Ga, Si, Ge, Sn, Pb, and Gd; and non-metallic elements, such as S. Specific content thereof is not particularly limited; however, the content of such other elements described above is preferably 10 wt. % or less relative to the amount of the fluorescent material for cosmetics.

The fluorescent material for cosmetics of an embodiment of the present invention may contain from 20 to 10000 ppm of potassium relative to the weight of the fluorescent material for cosmetics.

As described below in detail, in the fluorescent material for cosmetics of an embodiment of the present invention, the use of a potassium compound during production is preferable to perform efficient crushing and to achieve particle diameter that is required in the present invention. Such potassium used in the production process may remain. Even in such a case, the fluorescent material can be suitably used while the fluorescence characteristics and texture are not affected. The lower limit of the potassium amount described above is more preferably 50 ppm. The upper limit of the potassium amount described above is more preferably 5000 ppm and even more preferably 1000 ppm.

The average particle diameter of the fluorescent material for cosmetics of an embodiment of the present invention is from 1 to 10 μm. The lower limit of the average particle diameter described above is more preferably 2 μm and even more preferably 3 μm. The upper limit of the average particle diameter described above is more preferably 9 μm and even more preferably 8 μm.

Note that the average particle diameter in the present specification is a value measured by a method, in which the particle size distribution is measured by a laser diffraction particle size analyzer to calculate D50.

In the fluorescent material for cosmetics of an embodiment of the present invention, particles that are 30 μm or greater are preferably 15 vol. % or less in the volume-based particle size distribution curve measured by a laser diffraction particle size analyzer. When the fluorescent material satisfies the range described above, rough texture is less likely to be felt when the fluorescent material is applied to skin. Furthermore, in the particle diameter distribution, the particles having a particle diameter of 0.5 μm or less are preferably 10 vol. % or less. When the fluorescent material satisfies the range described above, a reduction in light emission intensity can be suppressed.

Note that the particle diameter distribution was measured by a laser diffraction particle size analyzer (MT3000, available from Nikkiso Co., Ltd.). At this time, the measurement was performed by mixing ion exchange water and a sample in a manner so that the diffraction volume (DV) is from 0.01 to 0.2.

In the fluorescent material for cosmetics of an embodiment of the present invention, D90/D50 is preferably 3 or less. The value of 3 or less is preferable from the perspective of achieving excellent texture of the particles, because the amount of coarse particles is sufficiently small. The D90 is a value measured by a method, in which the particle size distribution is measured by a laser diffraction particle size analyzer described above to calculate D90.

In the fluorescent material for cosmetics of an embodiment of the present invention, the BET specific surface area is preferably from 0.15 to 30 $m^2/g$. The range described above is preferable from the perspective of achieving high light emission intensity and excellent texture as cosmetics.

The sedimentation velocity of the fluorescent material particle of an embodiment of the present invention is preferably 5 cm/min or less. When the sedimentation velocity of the fluorescent material particle is in such a range, sedimentation of the fluorescent material particle can be suppressed in the case where the fluorescent material particle is used as a water-based dispersion cosmetic. The sedimentation velocity of the fluorescent material particle is more preferably 4 cm/min or less and even more preferably 1 cm/min or less. The sedimentation velocity of the fluorescent material particle can be measured by the method described in Examples described below.

The sedimentation velocity can be set to the range described above by adjusting the particle diameter, the particle density, the shape, the surface conditions, and the like.

The fluorescent material for cosmetics of an embodiment of the present invention may be a primary particle or an aggregate particle in which primary particles are aggregated. The aggregated particle is preferable from the perspective of ease in forming a particle with a large particle diameter and/or ease in forming a spherical shape.

For the fluorescent material for cosmetics of an embodiment of the present invention, the production method thereof is not particularly limited; however, for example, the production can be performed by mixing the compounds of elements constituting the fluorescent material for cosmetics of the embodiment of the present invention in predetermined proportions and then reduction-calcinating the mixture. Furthermore, as necessary, pre-calcinating, classification, water washing, crushing, and drying may be performed, or these steps (especially, pre-calcinating, classification, water washing, and crushing processes) may be repeated for twice or more, after the raw material compounds are mixed.

Furthermore, classification, water washing, and crushing may be performed after the reduction-calcinating. Furthermore, after the reduction calcinating, as necessary, a process of reduction-calcinating the particles, which have undergone classification, water washing, crushing, and the like, may be performed again for once or repeatedly for twice or more times.

The particles obtained by such process can achieve an average particle diameter of from 1 to 10 μm, which is suitable in an embodiment of the present invention.

In such a method of producing the fluorescent material for cosmetics, the used raw materials are not particularly limited, and examples thereof include the following substances.

Examples of the calcium source compound include carbonates, oxides, phosphates, chlorides, sulfates, nitrates, hydroxides, bromides, fluorides, iodides, organic acid salts, and borates of calcium, and the like. Among these, calcium carbonate, calcium phosphate, calcium acetate, calcium carbide, calcium chloride, calcium citrate, calcium hydrogen diphosphate, calcium dihydrogen phosphate, calcium diphosphate, calcium formate, calcium hydrogen phosphate, calcium hydroxide, calcium oxide, calcium hypophosphite, calcium oxalate, calcium nitrate, calcium peroxide, tricalcium phosphate, calcium phosphide, and calcium pyrophosphate are preferable. Calcium carbonate, calcium phosphate, calcium hydrogen diphosphate, calcium dihydrogen phosphate, calcium diphosphate, calcium hydrogen phosphate, calcium hydroxide, calcium oxide, calcium hypophosphite, tricalcium phosphate, and calcium pyrophosphate are particularly preferable. Furthermore, a combination of two or more types of these may be used.

Examples of the phosphorus source compound include phosphoric acids, phosphates, oxides, halides, and organic phosphorus compounds. Among these, phosphoric acids and/or phosphates are preferable. Among these, calcium phosphate, ammonium hydrogen phosphate, ammonium dihydrogen phosphate, diammonium hydrogen phosphate, phosphoric acid, phosphorous, calcium hydrogen diphosphate, calcium dihydrogen phosphate, calcium diphosphate, calcium hydrogen phosphate, calcium pyrophosphate, tricalcium phosphate, calcium phosphide, and calcium pyrophosphate are particularly preferable. Furthermore, a combination of two or more types of these may be used.

Examples of the cerium source compound include carbonates, chlorides, sulfates, nitrates, bromides, fluorides, hydroxides, and organic acid salts of cerium, and the like. Among these, cerium oxide, cerium carbonate, cerium chloride, and cerium nitrate are particularly preferable. Furthermore, the cerium source compound may be a compound containing a combination of two or more types of these.

In the preferable method of producing the fluorescent material for cosmetics of an embodiment of the present invention described above, first, the raw material compounds described above are mixed in proportions corresponding to the target composition.

The method of mixing these raw material compounds may be any known method. Examples of the mixing method include dry mixing, wet mixing, co-precipitation, and the like. Examples of the dry mixing include a mixing method that uses ordinary mixing apparatus, such as a Henschel mixer, tumbler, or V-blender, a hammer mill or a high-pressure air-jet mill, or a combination of these. Examples of the wet mixing include a method in which the raw material compound is formed into a water-based dispersion and agitated or mixed by a wet media mill, such as a bead mill or a planetary ball mill. If the entire amount is subjected to evaporative drying after the wet mixing, a powder mixture is obtained. The co-precipitation product can be obtained as a precipitate by neutralizing an aqueous solution of the raw material compounds.

Before the reduction-calcinating of the mixture obtained by the method described above, pre-calcinating may be performed. By performing the pre-calcinating, gases generated and originated from the raw material during reduction-calcinating (e.g. carbonic acid gas and the like) can be volatilized in advance. This is preferable because the effect on the calcinating atmosphere due to the gas originated from the raw materials can be reduced. The specific method of the pre-calcinating may be any known method. For example, the method may be a calcinating method that uses a ceramic crucible or a calcinating method that rotates the mixture by using a rotary kiln.

Furthermore, the pre-calcinating may be performed in the presence of a potassium compound. Such addition of potassium is preferable because a fluorescent material for cosmetics having the predetermined particle diameter can be easily obtained. That is, this is preferable because sintering during the calcinating and dry aggregation during the drying can be suppressed and because crushing performed in the following processes can be efficiently performed. Examples of the potassium compound that can be used include carbonates, oxides, phosphates, chlorides, sulfates, nitrates, hydroxides, bromides, fluorides, iodides, organic acid salts, and borates of potassium, and the like. Among these, potassium carbonate, potassium chloride, potassium citrate, potassium dihydrogen phosphate, potassium diphosphate, potassium hydrogen carbonate, and potassium hydroxide are particularly preferable.

In the case where a potassium compound is added, the added amount thereof is preferably from 50 to 10000 ppm in terms of potassium amount relative to the weight of the obtained fluorescent material for cosmetics. Such an amount can suitably achieve the effects described above. The lower limit of the potassium amount described above is more preferably 60 ppm and even more preferably 70 ppm. The upper limit of the potassium amount described above is more preferably 7000 ppm and even more preferably 5000 ppm.

The atmosphere of the pre-calcinating described above is not particularly limited and may be an oxidative atmosphere, reducing atmosphere, inert atmosphere, or the like. The atmosphere gas may be appropriately selected, and for example, the air, carbon dioxide, oxygen, hydrogen, nitrogen, argon, a mixture gas of these, or the like can be used.

The pre-calcinating may be performed in an oxidative calcinating condition, such as calcinating in the air, may be performed in an inert atmosphere, such as nitrogen or argon, may be performed in a carbon dioxide atmosphere, or may be performed in a reducing atmosphere. The calcinating temperature is not particularly limited but is preferably from 500 to 1600° C. The pre-calcinating is more preferably performed at from 600 to 1550° C. A temperature of 500° C. or higher is preferable because the volatiles can be sufficiently volatilized from the raw materials and because change in the atmosphere during the following reduction calcinating can be sufficiently prevented. A temperature of 1600° C. or lower is preferable because excessive sintering can be suppressed and excellent dispersibility can be achieved when the fluorescent material is used in cosmetics.

As necessary, the particles after the pre-calcinating may be subjected to classification by a sieve, washing by water or acid or alkali, crushing, and the like. Furthermore, after the pre-calcinating, as necessary, a process of pre-calcinating the particles, which have undergone classification, water washing, crushing, and the like, may be performed again for once or repeatedly for twice or more times. In particular, the particles obtained after repeating the process of pre-calcinating the particles after the pre-calcinating again for once or twice or more times are preferable from the perspective of enhancing light emission intensity.

In the method described above, the particles after undergoing the pre-calcinating may be subjected to crushing. Performing crushing before the reduction calcinating is performed as described above is preferable because the raw materials are more uniformly mixed. This process can be performed by a publicly known method, such as wet crushing (e.g. crushing using a wet media mill, such as a bead mill or a planetary ball mill) and dry crushing (e.g. a hammer mill or a high-pressure air-jet mill).

Furthermore, a potassium compound may be added before or after the crushing or during the crushing described above. Such addition of a potassium compound is preferable because a fluorescent material for cosmetics having the predetermined particle diameter can be easily obtained. The added amount and the compound that can be used in this case are the same as those of the case where addition is performed before the pre-calcinating described above.

Reduction calcinating is preferably performed after the process of mixing the raw material compounds in proportions corresponded to the target composition, and then optional processes described above are performed as needed.

This is preferable because a fluorescent material for cosmetics having the predetermined particle diameter and having high luminance can be obtained.

The specific method of the calcinating in a reducing condition is not particularly limited and may be an ordinary method. Examples thereof include a hydrogen-containing atmosphere. As the hydrogen-containing atmosphere, for example, the calcinating can be performed in a nitrogen atmosphere containing from 0.01 to 40 vol. % of hydrogen.

The calcinating temperature is not particularly limited but is preferably from 1150 to 1600° C. The calcinating is more preferably performed at 1200 to 1550° C. A calcinating temperature of 1150° C. or higher is preferable because a compound of a desired fluorescent material having $Ca_aP_bO_c$ can be produced efficiently and because a fluorescent material emitting light with sufficiently high luminance can be obtained. A temperature of 1600° C. or lower is preferable because excessive sintering can be suppressed and because excellent dispersibility can be achieved when the fluorescent material is used in cosmetics.

After the reduction calcinating described above, as necessary, classification by a sieve, washing by water or acid or alkali, crushing, and the like may be performed. Furthermore, after the reduction calcinating, as necessary, a process of reduction-calcinating the particles, which have undergone classification, water washing, crushing, and the like, may be performed again for once or repeatedly for twice or more times.

The fluorescent material for cosmetics of an embodiment of the present invention can be blended into cosmetics as is;

however, as necessary, the fluorescent material may be blended after undergoing known various surface treatments. In particular, water resistance is preferably enhanced by subjecting the fluorescent material for cosmetics of an embodiment of the present invention to a hydrophobic surface treatment.

The type of the surface treatment is not particularly limited and may be treated by using any substance that can be used in cosmetics. For example, a coating layer composed of an inorganic compound, such as oxides, hydroxides, carbonates, and phosphates of silicon, zinc, titanium, aluminum, zirconium, and tin may be provided. Furthermore, to impart water repellency, dimethylpolysiloxane, methylhydrogenpolysiloxane, methylphenylpolysiloxane, methylmethoxypolysiloxane, dimethylpolysiloxane dihydrogen, and copolymers thereof; stearic acid, lauric acid, oleic acid, and metal salts thereof (aluminum salt, zinc salt, magnesium salt, calcium salt, and the like); polyvinyl alcohol, ethylene glycol, propylene glycol, monoethanolamine, aminomethylpropanol, diethanolamine, triethanolamine, monopropanolamine, dipropanolamine, tripropanolamine, paraffin wax, polyethylene wax, aminosilane, epoxysilane, methacrylsilane, vinylsilane, mercaptosilane, chloroalkylsilane, alkylsilane, fluoroalkylsilane, hexamethylsilazane, hexamethylcyclotrisilazane, trimethylolpropane, trimethylolethane, and pentaerythritol can be used.

Furthermore, for these surface treatments, lamination or combined treatment may be performed by one type or a combination of two or more types. Furthermore, a coating layer of an organic compound may be provided after or before the treatment by an inorganic compound, but it is important not to deteriorate the original light emission property.

The coated amount of the inorganic compound and the organic compound is preferably in the range of 0.1 to 30 wt. % and more preferably in the range of 0.1 to 20 wt. %, relative to the amount of the fluorescent material for cosmetics after the coating. The coated amount of 0.1 wt. % or greater can suitably exhibit effects of enhancing functionality by the surface treatment. Furthermore, the coated amount of 30 wt. % or less enables the treatment without losing the original light emission characteristics and is advantageous from the perspective of economy.

The surface treatment method is not particularly limited, but examples thereof include wet methods and dry methods. Examples of the wet method include a method in which the surface of the fluorescent material is treated with an inorganic compound or an organic compound in a water solvent or an organic solvent. More specifically, coating can be performed by adding an inorganic compound or an organic compound into an aqueous dispersion of the fluorescent material for cosmetics and then adjusting the pH. Furthermore, as another specific method, coating can be performed by adding the fluorescent material for cosmetics in an aqueous solution of an inorganic compound to coat, performing crushing or mixing as necessary, and then adjusting the pH. Furthermore, as another specific method, coating can be performed by adding an inorganic compound or an organic compound and the fluorescent material in an aqueous solvent in which the pH is adjusted to high in advance, performing crushing or mixing as necessary, and then adjusting the pH.

Furthermore, as a wet surface treatment method, another publicly known method can be applied besides the method by pH adjustment described above. More specific examples thereof include a method in which coating is performed by adding an inorganic compound or an organic compound into an aqueous or organic solvent dispersion of the fluorescent material for cosmetics and then volatilizing the solvent; and the like.

Examples of the dry method include a method in which the fluorescent material surface is treated with a water solvent or an organic solvent to which an inorganic compound or an organic compound is added. More specific examples thereof include a method in which a water solvent or an organic solvent to which an inorganic compound or an organic compound is added is added to the fluorescent material by spraying or the like and mixed. Furthermore, to coat an organic compound that is not water soluble, the surface treatment can be performed by adding the organic compound by a dry method, crushing and mixing, and heating as necessary.

Another embodiment of the present invention is a cosmetic containing the fluorescent material for cosmetics described above.

The cosmetic of an embodiment of the present invention preferably contains from 0.1 to 90 wt. % of the fluorescent material for cosmetics described above. When the content is less than 0.1 wt. %, the effect may not be sufficiently achieved. The content of greater than 90 wt. % may be disadvantageous because the amount of the powder becomes excessive, thus reducing the degree of freedom of blending as a cosmetic, such as making it impossible to sufficiently blend a liquid component, and the handling may be deteriorated. The content described above is more preferably from 0.1 to 50 wt. %, and even more preferably from 0.1 to 30 wt. %.

Examples of the cosmetic of an embodiment of the present invention include foundations, makeup bases, eye shadows, blushers, mascaras, lipsticks, sunscreen agents, and the like. The cosmetic of an embodiment of the present invention may be in any form selected from an oil-based cosmetic, a water-based cosmetic, an O/W cosmetic, or a W/O cosmetic. Among these, the present invention can be suitably applied especially in makeup cosmetics, such as foundations, makeup bases, and eye shadows; and sunscreen agents.

In the cosmetic of an embodiment of the present invention, any aqueous component or oily component that can be used in the field of cosmetics can be used in combination in addition to the fluorescent material for cosmetics described above. The aqueous component and oily component described above are not particularly limited. Examples thereof may include those containing components such as oils, surfactants, moisturizers, higher alcohols, sequestrants, natural and synthetic polymers, water-soluble and oil-soluble polymers, ultraviolet blocking agents, various extracts, inorganic and organic pigments, inorganic and organic clay minerals and other powders, inorganic and organic pigments that are metallic soap-treated or silicone-treated, coloring materials such as organic dyes; preservatives, antioxidants, dyes, thickeners, pH adjusters, perfumes, cooling-sensation agents, antiperspirants, disinfectants, and skin activators. Furthermore, another fluorescent material for cosmetics besides the fluorescent material for cosmetics of the present invention may be contained. Specifically, a desired cosmetic can be produced in the usual manner using any one or two or more types of the ingredients listed below. The compounded amounts of these ingredients are not particularly limited as long as the compounded amounts are in the range that do not impair the effect of the present invention.

The oil is not particularly limited. Examples thereof may include *avocado* oil, *Camellia* oil, turtle oil, *Macadamia* nut oil, corn oil, mink oil, olive oil, rapeseed oil, egg-yolk oil, sesame oil, persic oil, wheat germ oil, *Sasanqua* oil, castor oil, linseed oil, safflower oil, cottonseed oil, *Perilla* oil, soybean oil, *Arachis* oil, tea seed oil, *Kaya* oil, rice bran oil, Chinese tung oil, Japanese tung oil, *jojoba* oil, germ oil, triglycerol, glycerol trioctanoate, glycerol triisopalmitate, cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, neatsfoot oil, Japan wax, hydrogenated castor oil, beeswax, *candelilla* wax, cotton wax, carnauba wax, bayberry wax, insect wax, spermaceti wax, montan wax, bran wax, lanolin, kapok wax, lanolin acetate, liquid lanolin, sugarcane wax, lanolin fatty acid isopropyl ester, hexyl laurate, reduced lanolin, *jojoba* wax, hard lanolin, shellac wax, POE lanolin alcohol ether, POE lanolin alcohol acetate, POE cholesterol ether, lanolin fatty acid polyethylene glycol ester, POE hydrogenated lanolin alcohol ether, liquid paraffin, ozokerite, pristane, paraffin, ceresin, squalene, vaseline, microcrystalline wax, and the like.

The surfactant described above is not particularly limited. Examples thereof include lipophilic nonionic surfactants, hydrophilic nonionic surfactants, and other surfactants.

The lipophilic nonionic surfactant described above is not particularly limited. Examples thereof may include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerin polyglycerin fatty acid esters, such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters, such as propylene glycol monostearate; hydrogenated castor oil derivatives; glycerol alkyl ethers; and the like.

The hydrophilic nonionic surfactant described above is not particularly limited. Examples thereof may include POE sorbitan fatty acid esters, such as POE sorbitan monooleate, POE sorbitan monostearate, and POE sorbitan tetraoleate; POE sorbitol fatty acid esters, such as POE sorbitol monolaurate, POE sorbitol monooleate, POE sorbitol pentaoleate, and POE sorbitol monostearate; POE glycerin fatty acid esters, such as POE glycerin monostearate, POE glycerin monoisostearate, and POE glycerin triisostearate; POE fatty acid esters, such as POE monooleate, POE distearate, POE monodioleate, and ethylene glycol distearate; POE alkyl ethers, such as POE lauryl ether, POE oleyl ether, POE stearyl ether, POE behenyl ether, POE 2-octyldodecyl ether, and POE cholestanol ether; POE alkyl phenyl ethers, such as POE octyl phenyl ether, POE nonyl phenyl ether, and POE dinonyl phenyl ether; Pluaronic types, such as Pluronic; POE/POP alkyl ethers, such as POE/POP cetyl ether, POE/POP 2-decyltetradecyl ether, POE/POP monobutyl ether, POE/POP hydrogenated lanolin, and POE/POP glycerin ether; tetra-POE/tetra-POP ethylenediamine condensation products, such as Tetronic; POE castor oil; POE hydrogenated castor oil derivatives such as POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleic acid; POE beeswax/lanolin derivatives, such as POE sorbitol beeswax; alkanolamides, such as coconut oil fatty acid diethanolamide, lauric acid monoethanolamide, and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; trioleyl phosphoric acid; and the like.

Other surfactants described above may be compounded in the range that does not cause any problems in stability and skin irritation. Examples thereof include anionic surfactants, such as fatty acid soaps, higher-alkyl sulfuric ester salts, POE triethanolamine lauryl sulfate, and alkyl ether sulfuric ester salts; cationic surfactants, such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants, such as imidazoline amphoteric surfactants and betaine surfactants.

The moisturizer described above is not particularly limited. Examples thereof may include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerol (EO) PO adducts, *Rosa roxburghii* extract, yarrow extract, melilot extract, and the like.

The higher alcohol described above is not particularly limited. Examples thereof may include linear alcohols such as lauryl alcohol, cetyl alcohol, stearyl alcohol, behenyl alcohol, myristyl alcohol, oleyl alcohol, and cetostearyl alcohol; branched alcohols such as monostearyl glycerol ether (batyl alcohol), 2-decyltetradecynol, lanolin alcohol, cholesterol, phytosterol, hexyldodecanol, isostearyl alcohol, and octyldodecanol; and the like.

The sequestrant is not particularly limited. Examples thereof may include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, edetic acid, and the like.

The natural water-soluble polymer described above is not particularly limited. Examples thereof may include plant-derived polymers, such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers, such as xanthan gum, dextran, succinoglucan, and pullulan; and animal-derived polymers, such as collagen, casein, albumin, and gelatin.

The semisynthetic water-soluble polymer is not particularly limited. Examples thereof may include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethylcellulose (CMC), crystalline cellulose, and cellulose powder; alginate polymers such as sodium alginate and propylene glycol alginate; and the like.

The synthetic water-soluble polymer is not particularly limited. Examples thereof may include vinyl polymers, such as polyvinyl alcohol, polyvinyl methyl ether, and polyvinyl pyrrolidone; polyoxyethylene polymers, such as polyethylene glycol 20000, polyethylene glycol 40000, and polyethylene glycol 60000; polyoxyethylene-polyoxypropylene copolymers; acrylic polymers, such as sodium polyacrylate, polyethylacrylate, and polyacrylamide; polyethyleneimine; cationic polymers; and the like.

The inorganic water-soluble polymer is not particularly limited. Examples thereof may include bentonite, AlMg silicate (Veegum), laponite, hectorite, silicic anhydride, and the like.

The ultraviolet blocking agent is not particularly limited. Examples thereof may include benzoic acid-based ultraviolet blocking agents, such as paraaminobenzoic acid (hereinafter, abbreviated as "PABA"), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid-based ultraviolet blocking agents, such as homomenthyl-N-acetyl anthranilate; salicylic acid-based ultraviolet blocking agents, such as amyl salicylate, menthyl salicylate, homomenthyl salicylate, octyl salicylate, phenyl salicylate, benzyl salicylate, and p-isopropanol phenyl salicylate; cinnamic acid-based ultraviolet blocking agents, such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxy ethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl-mono-2-ethylhexanoyl-diparamethoxy cinnamate; benzophenone-based ultraviolet blocking agents, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, 5-(3,3-dimethyl-2-norbornylidene)-3-pentan-2-one, and the like.

Other chemical components are not particularly limited, and examples thereof include vitamins, such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones, such as estradiol and ethynyl estradiol; amino acids, such as arginine, aspartic acid, cystine, cysteine, methionine, serine, leucine, and tryptophan; anti-inflammatory agents, such as allantoin and azulene; whitening agents, such as arbutin; astringents, such as tannic acid; refrigerants, such as L-menthol and camphor, sulfur, lysozyme chloride, and pyridoxine chloride; and the like.

Various kinds of extracts are not particularly limited. Examples thereof may include *Houttuynia cordata* extract, *Phellodendron* bark extract, melilot extract, dead nettle extract, licorice extract, peony root extract, soapwort extract, *Luffa* extract, *Cinchona* extract, strawberry *Geranium* extract, *Sophora* root extract, *Nuphar* extract, fennel extract, primrose extract, rose extract, *Rehmannia* root extract, lemon extract, *Lithospermum* root extract, *Aloe* extract, *Calamus* root extract, *Eucalyptus* extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, *Hamamelis* extract, placenta extract, thymic extract, silk extract, licorice extract, and the like.

Examples of the various kinds of powders described above may include bright coloring pigments, such as red oxide, yellow iron oxide, black iron oxide, mica titanium, iron oxide-coated mica titanium, and titanium oxide-coated glass flakes; inorganic powders, such as those of mica, talc, kaolin, sericite, titanium dioxide, and silica; organic powders, such as polyethylene powder, nylon powder, cross-linked polystyrene, cellulose powder, and silicone powder; and the like. Preferably, for enhancing sensory characteristics and makeup retainability, a part or all of the powder component may be subjected to a hydrophobization treatment and be used by a publicly known method using a substance such as a silicone, a fluorine compound, a metallic soap, an oily agent, or an acyl glutamic acid salt.

EXAMPLES

The present invention will be described hereinafter with reference to examples, but the present invention is not limited to these examples.

Method of Producing Fluorescent Material for Cosmetics

Example 1

10.51 g of calcium carbonate (product name "CWS-20", available from Sakai Chemical Industry Co., Ltd.), 0.17 g of cerium oxide (available from Shin-Etsu Chemical Co., Ltd.), and 12.71 g of calcium pyrophosphate (available from Taihei Ceramic Industry Pharmaceuticals Co., Ltd.) were weighed and dry-mixed. Then, the mixture was charged in an alumina crucible, the temperature was increased to 850° C. at 200° C./h in the air atmosphere and then maintained as is for 3 hours, and then the temperature was decreased at 200° C./h. The fired powder was sufficiently mixed and crushed by using a planetary ball mill. The crushed slurry was subjected to evaporative drying overnight in a dryer at 130° C. to obtain a dried powder. The dried powder was then charged in an alumina crucible, the temperature was increased to 1400° C. at 200° C./h in the nitrogen atmosphere having 3 vol. % of hydrogen and then maintained as is for 8 hours, and then the temperature was decreased at 200° C./h. The fired powder was crushed by using a planetary ball mill. Therefore, a fluorescent material P1 having an average particle diameter of 5.1 µm was obtained.

Figure 1:
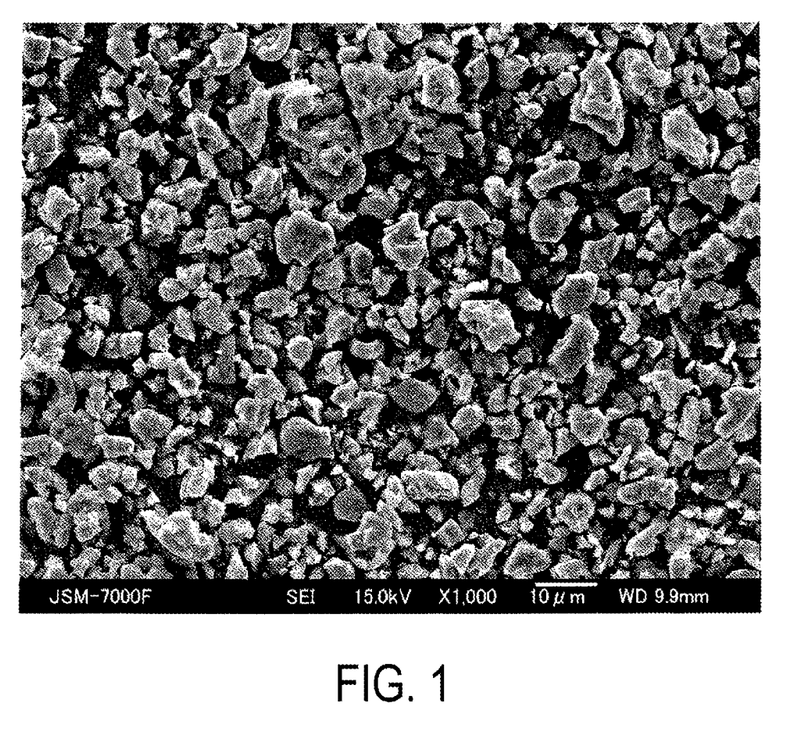
FIG. 1 is an electron micrograph of the fluorescent material P1 obtained in Example 1.

The electron micrograph of the obtained P1 is shown in FIG. 1.

Note that, when the results of the analyzed composition of P1 are applied in the general formula of the claim 1, $a=4.08$, $b=2.00$, and $c=9.08$. Ce was 0.01 relative to 1 mol of the phosphorous. The composition analysis of the fluorescent material was performed by using an ICP optical emission spectrometer (SPS1700 HVR, available from Seiko Instruments Inc.). The analysis was performed in the same manner in the following Examples.

Example 2

16.21 g of calcium carbonate (product name "CWS-20", available from Sakai Chemical Industry Co., Ltd.), 0.14 g of cerium oxide (available from Shin-Etsu Chemical Co., Ltd.), 9.37 g of ammonium dihydrogen phosphate (reagent), and 0.052 g of potassium carbonate (reagent) were weighed and sufficiently mixed and crushed by using a planetary ball mill. The mixture slurry was subjected to evaporative drying overnight in a dryer at 130° C. to obtain a dried powder. The dried powder was then charged in an alumina crucible, the temperature was increased to 1400° C. at 200° C./h in the nitrogen atmosphere having 3 vol. % of hydrogen and then maintained as is for 8 hours, and then the temperature was decreased at 200° C./h. The fired powder was crushed by using a planetary ball mill. Therefore, a fluorescent material P2 having an average particle diameter of 6.8 μm was obtained.

Figure 2:
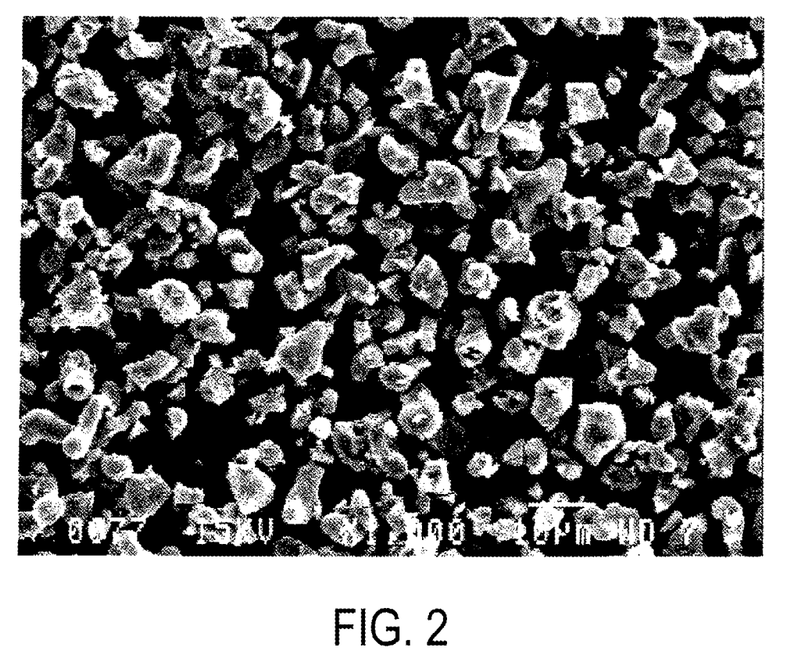
FIG. 2 is an electron micrograph of the fluorescent material P2 obtained in Example 2.

The electron micrograph of the obtained P2 is shown in FIG. 2.

Note that, when the results of the analyzed composition of P2 are applied in the general formula of the claim 1, a=3.67, b=2.00, and c=8.67. Ce was 0.009 relative to 1 mol of the phosphorous. K was 54 ppm.

Example 3

1.72 kg of calcium carbonate (product name "CWS-20", available from Sakai Chemical Industry Co., Ltd.), 28 g of cerium oxide (available from Shin-Etsu Chemical Co., Ltd.), and 2.08 kg of calcium pyrophosphate (available from Taihei Ceramic Industry Pharmaceuticals Co., Ltd.) were weighed and mixed by using a V-blender. Then, the mixture was charged in an alumina sagger, the temperature was increased to 1200° C. at 150° C./h in the air atmosphere and then maintained as is for 5 hours, and then the temperature was decreased at 150° C./h. The fired powder, 12 g of potassium carbonate (reagent), ion exchange water, and alumina balls were charged in a bead mill and sufficiently mixed and crushed by using the bead mill. The crushed slurry was dried by a spray dryer to obtain a dried powder. Then, the dried powder was charged in an alumina sagger, the temperature was increased to 1300° C. at 150° C./h in the nitrogen atmosphere having 3 vol. % hydrogen and then maintained as is for 8 hours, and then the temperature was decreased at 150° C./h. The fired powder was crushed by using a high-pressure air-jet mill. Therefore, a fluorescent material P3 having an average particle diameter of 4.5 μm was obtained.

Figure 3:
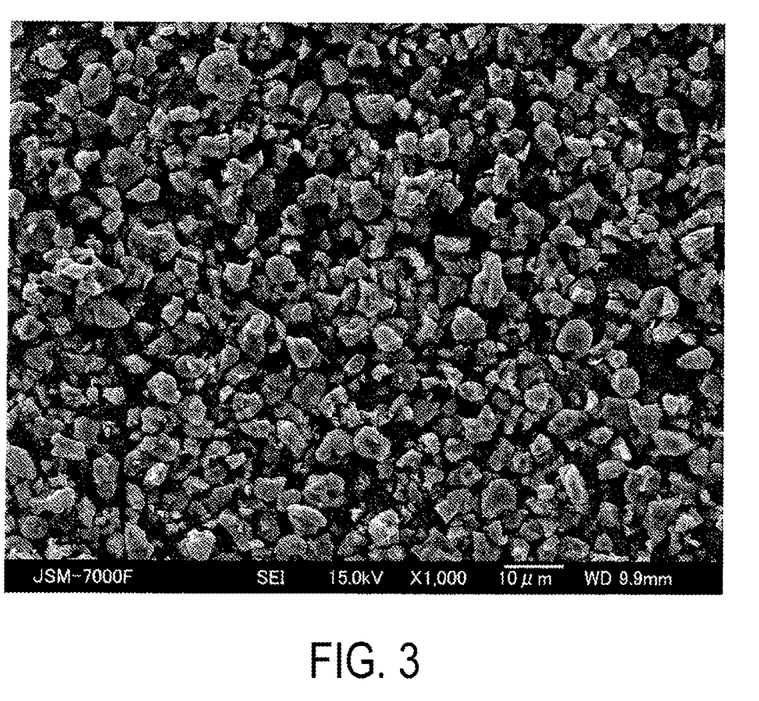
FIG. 3 is an electron micrograph of the fluorescent material P3 obtained in Example 3.

The electron micrograph of the obtained P3 is shown in FIG. 3.

Note that, when the results of the analyzed composition of P3 are applied in the general formula of the claim 1, a=4.02, b=2.00, and c=9.02. Ce was 0.01 relative to 1 mol of the phosphorous. K was 489 ppm.

Example 4

10.51 g of calcium carbonate (product name "CWS-20", available from Sakai Chemical Industry Co., Ltd.), 0.085 g of cerium oxide (available from Shin-Etsu Chemical Co., Ltd.), and 12.71 g of calcium pyrophosphate (available from Taihei Ceramic Industry Pharmaceuticals Co., Ltd.) were weighed and dry-mixed. Then, the mixture was charged in an alumina crucible, the temperature was increased to 850° C. at 200° C./h in the air atmosphere and then maintained as is for 3 hours, and then the temperature was decreased at 200° C./h. The fired powder was sufficiently mixed and crushed by using a planetary ball mill. The crushed slurry was subjected to evaporative drying overnight in a dryer at 130° C. to obtain a dried powder. The dried powder was then charged in an alumina crucible, the temperature was increased to 1400° C. at 200° C./h in the nitrogen atmosphere having 0.3 vol. % of hydrogen and then maintained as is for 8 hours, and then the temperature was decreased at 200° C./h. The fired powder was crushed by using a planetary ball mill. Therefore, a fluorescent material P4 having an average particle diameter of 5.3 μm was obtained.

Note that, when the results of the analyzed composition of P4 are applied in the general formula of the claim 1, a=4.07, b=2.00, and c=9.07. Ce was 0.005 relative to 1 mol of the phosphorous.

Example 5

10.51 g of calcium carbonate (product name "CWS-20", available from Sakai Chemical Industry Co., Ltd.), 0.26 g of cerium oxide (available from Shin-Etsu Chemical Co., Ltd.), and 12.71 g of calcium pyrophosphate (available from Taihei Ceramic Industry Pharmaceuticals Co., Ltd.) were weighed and dry-mixed. Then, the mixture was charged in an alumina crucible, the temperature was increased to 850° C. at 200° C./h in the air atmosphere and then maintained as is for 3 hours, and then the temperature was decreased at 200° C./h. The fired powder was sufficiently mixed and crushed by using a planetary ball mill. The crushed slurry was subjected to evaporative drying overnight in a dryer at 130° C. to obtain a dried powder. The dried powder was then charged in an alumina crucible, the temperature was increased to 1400° C. at 200° C./h in the nitrogen atmosphere having 0.3 vol. % of hydrogen and then maintained as is for 8 hours, and then the temperature was decreased at 200° C./h. The fired powder was crushed by using a planetary ball mill. Therefore, a fluorescent material P5 having an average particle diameter of 4.9 μm was obtained.

Note that, when the results of the analyzed composition of P5 are applied in the general formula of the claim 1, a=4.05, b=2.00, and c=9.05. Ce was 0.015 relative to 1 mol of the phosphorous.

Comparative Example 1

10.51 g of calcium carbonate (product name "CWS-20", available from Sakai Chemical Industry Co., Ltd.), 0.17 g of cerium oxide (available from Shin-Etsu Chemical Co., Ltd.), and 12.71 g of calcium pyrophosphate (available from Taihei Ceramic Industry Pharmaceuticals Co., Ltd.) were weighed and dry-mixed. Then, the mixture was charged in an alumina crucible, the temperature was increased to 850° C. at 200° C./h in the air atmosphere and then maintained as is for 3 hours, and then the temperature was decreased at 200° C./h. The fired powder was sufficiently mixed and crushed by using a planetary ball mill. The crushed slurry was subjected to evaporative drying overnight in a dryer at 130° C. to obtain a dried powder. The dried powder was then charged in an alumina crucible, the temperature was increased to 1605° C. at 200° C./h in the nitrogen atmosphere having 3 vol. % of hydrogen and then maintained as is for 2 hours, and then the temperature was decreased at 200° C./h. Therefore, a fluorescent material Q1 having an average particle diameter of 110.5 μm was obtained.

Figure 4:
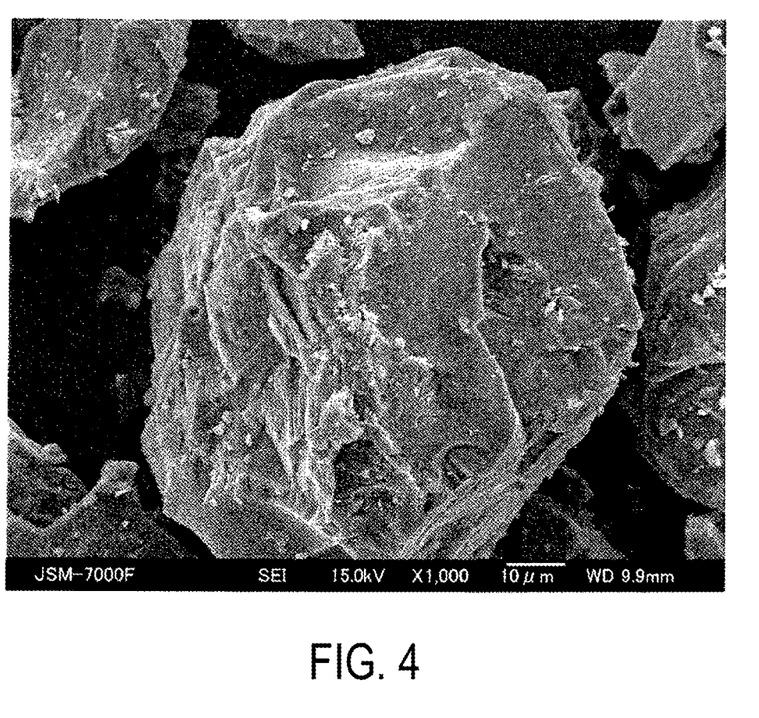
FIG. 4 is an electron micrograph of the fluorescent material Q1 obtained in Comparative Example 1.

The electron micrograph of the obtained Q1 is shown in FIG. 4.

Note that, when the results of the analyzed composition of Q1 are applied in the general formula of the claim 1, a=4.09, b=2.00, and c=9.09. Ce was 0.01 relative to 1 mol of the phosphorous.

Comparative Example 2

1.72 kg of calcium carbonate (product name "CWS-20", available from Sakai Chemical Industry Co., Ltd.), 28 g of cerium oxide (available from Shin-Etsu Chemical Co., Ltd.), and 2.08 kg of calcium pyrophosphate (available from Taihei Ceramic Industry Pharmaceuticals Co., Ltd.) were weighed and mixed by using a V-blender. Then, the mixture was charged in an alumina sagger, the temperature was increased to 1200° C. at 150° C./h in the air atmosphere and then maintained as is for 5 hours, and then the temperature was decreased at 150° C./h. The fired powder, 12 g of potassium carbonate (reagent), ion exchange water, and alumina balls were charged in a bead mill and sufficiently mixed and crushed by using the bead mill. The crushed slurry was dried by a spray dryer to obtain a dried powder. The dried powder was then charged in an alumina crucible, the temperature was increased to 1100° C. at 200° C./h in the nitrogen atmosphere having 3 vol. % of hydrogen and then maintained as is for 8 hours, and then the temperature was decreased at 200° C./h. The fired powder was crushed by using a planetary ball mill. Therefore, a fluorescent material Q2 having an average particle diameter of 0.72 μm was obtained.

Figure 5:
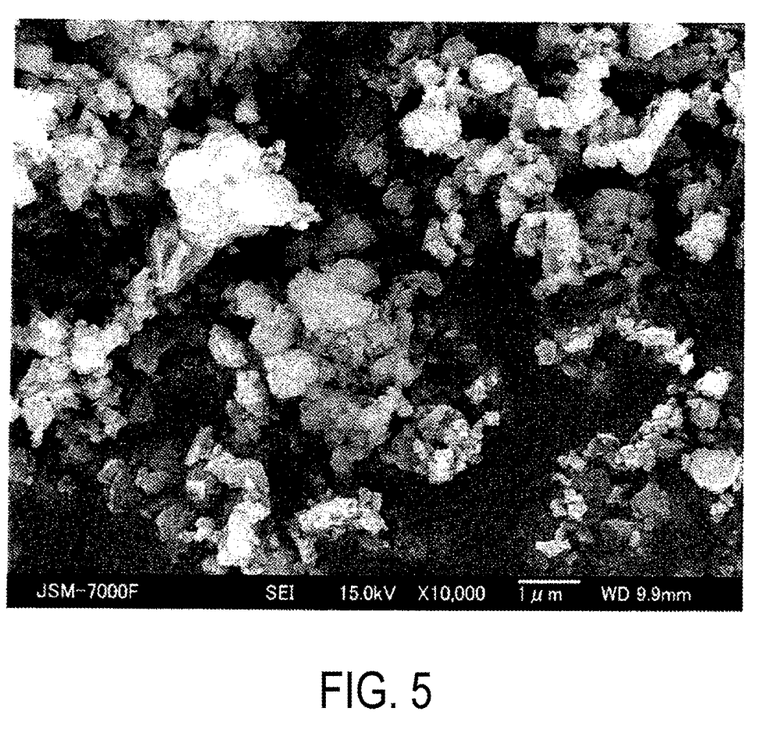
FIG. 5 is an electron micrograph of the fluorescent material Q2 obtained in Comparative Example 2.

The electron micrograph of the obtained Q2 is shown in FIG. 5.

Note that, when the results of the analyzed composition of Q2 are applied in the general formula of the claim 1, a=4.02, b=2.00, and c=9.02. Ce was 0.01 relative to 1 mol of the phosphorous. K was 489 ppm.

Evaluation Example 1 (Evaluation as Fluorescent Material)

The fluorescent material samples obtained in Examples and Comparative Examples were evaluated.
Measurement of Excitation Spectrum and Emission Spectrum The measurement of excitation spectrum and emission spectrum was performed by using a spectrofluorophotometer (FP-6500, available from JASCO Corporation). As the fluorescence integrating sphere, ISF-513 was used, and the voltage of photomultiplier (PMT) was set to 340. The excitation spectrum is a spectrum that measured light emission intensity by scanning the wavelength of the excitation light while the light emission wavelength is fixed. The emission spectrum is a spectrum that measured light emission intensity while the wavelength of the excitation light is fixed.

Figure 6:
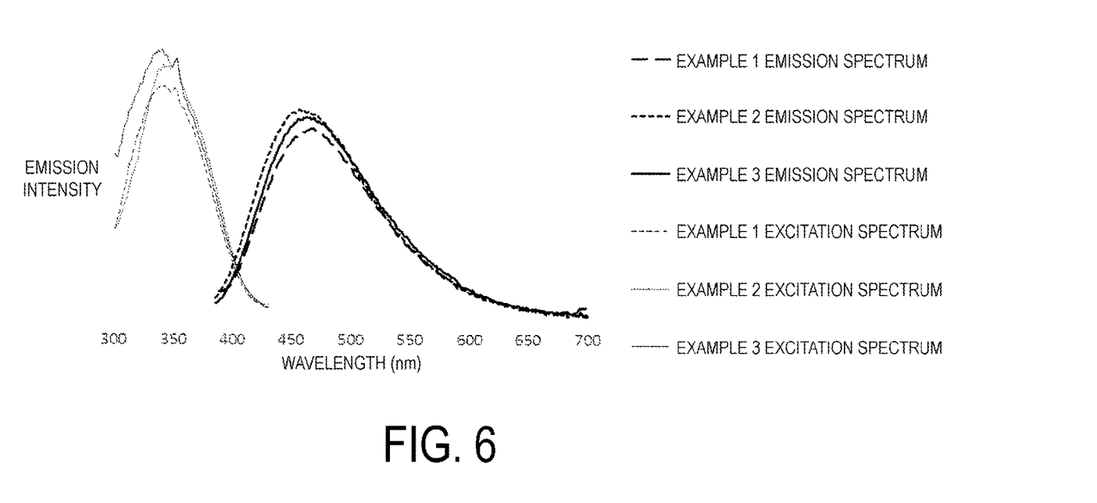
FIG. 6 is a diagram showing the emission spectra and the excitation spectra of the fluorescent materials obtained in Examples 1 to 3.

FIG. 6 shows, for P1 to P3 obtained in Examples 1 to 3, the excitation spectra at the time when the light emission wavelength were 460 nm and the emission spectra at the time when the excitation light having the wavelength of 365 nm were irradiated.

Figure 7:
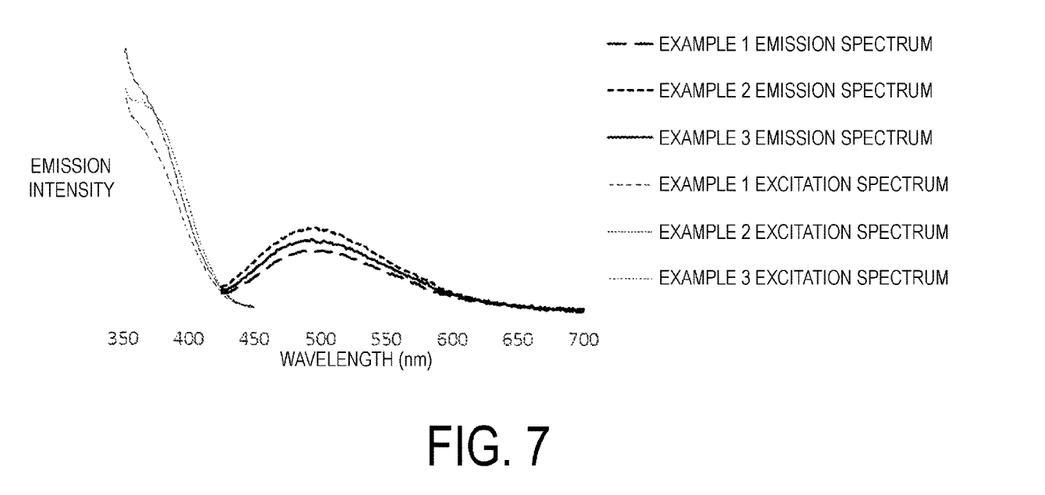
FIG. 7 is a diagram showing the emission spectra and the excitation spectra of the fluorescent materials obtained in Examples 1 to 3.

Furthermore, FIG. 7 shows, for P1 to P3 obtained in Examples 1 to 3, the excitation spectra at the time when the light emission wavelength were 495 nm and the emission spectra at the time when the excitation light having the wavelength of 405 nm were irradiated.
Measurement of Luminance Y and Chromaticity (x, y)

The results obtained in the measurement of emission spectra described above were analyzed by using a color analysis software for emitted light of FP-6500, available from JASCO Corporation, to evaluate the luminance Y and chromaticity (x, y).

Table 1 shows the results of evaluation of the emission spectra when the excitation light having the wavelength of 365 nm was irradiated, for P1 to P5 and Q1 and Q2 obtained in Examples 1 to 5 and Comparative Examples 1 and 2.

Furthermore, Table 2 shows the results of evaluation of the emission spectra when the excitation light having the wavelength of 405 nm was irradiated, for P1 to P3 obtained in Examples 1 to 3.
Measurement of Dominant Wavelength Smoothing was performed for the results obtained in the measurement of the emission spectra described above, and then the dominant wavelength (maximum light emission wavelength) and the light emission intensity were determined by peak detection. As the light emission intensity at this time, relative light emission intensities of P2 to P5 and Q1 and Q2 were determined taking the light emission intensity at the time when the fluorescent material P1 obtained in Example 1 was irradiated with the excitation light having the wavelength of 365 nm as 100.

Table 1 shows the evaluation results of the dominant wavelengths and the light emission intensities of the emission spectra when the excitation light having the wavelength of 365 nm was irradiated, for P1 to P5 and Q1 and Q2 obtained in Examples 1 to 5 and Comparative Examples 1 and 2.

Furthermore, Table 2 shows the evaluation results of the dominant wavelengths and the light emission intensities of the emission spectra when the excitation light having the wavelength of 405 nm was irradiated, for P1 to P3 obtained in Examples 1 to 3.
Shape of Fluorescent Material Particle The shape and the size of the fluorescent material particle were measured by using a scanning electron microscope (SEM) (7000F, available from JEOL Ltd.). FIGS. 1 to 5 show the results of the taken scanning electron micrographs of the fluorescent materials P1 to P3 obtained in Examples 1 to 3 and the fluorescent materials Q1 and Q2 obtained in Comparative Examples 1 and 2.
Identification of Fluorescent Material Measurement of X-ray powder diffraction pattern was performed by using an X-ray powder diffraction (XRD) instrument (available from Rigaku Corporation; RINT-TTRIII; X-ray=CuKα, λ=1.5406 □, 50 kV, 300 mA) to identify the product.

Figure 8:
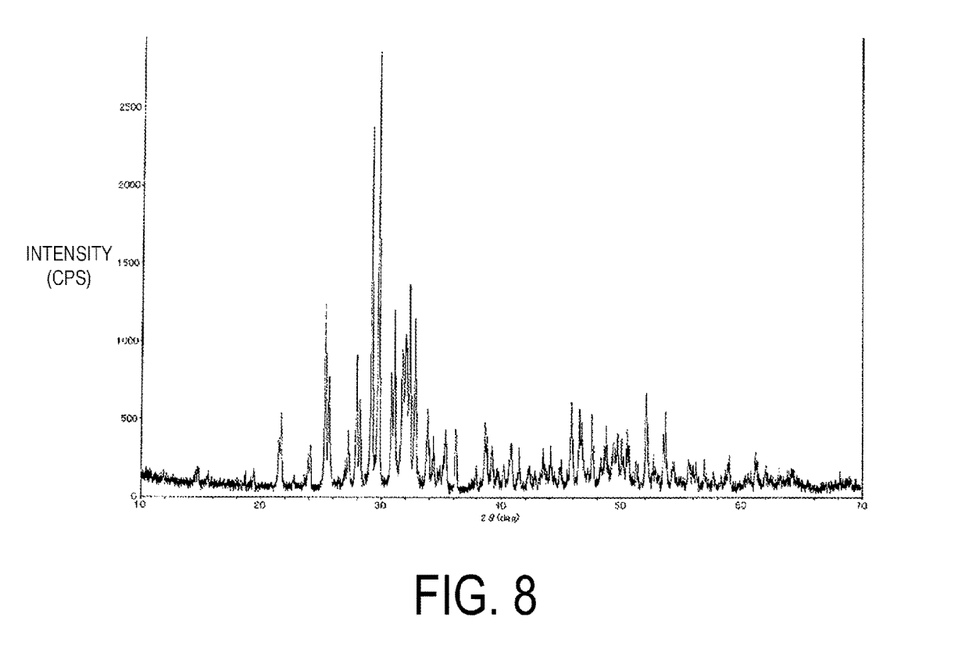
FIG. 8 is a diagram showing a result of X-ray powder diffraction of the fluorescent material obtained in Example 1.

FIG. 8 shows the measurement result of P1 obtained in Example 1. The results obtained by measuring P2 to P5 and Q1 in the same manner as for P1 showed that each of the X-ray powder diffraction patterns of P1 to P5 and Q1 is identical with the PDF card #00-025-1137, and it was confirmed that the base compositions of P1 to P5 and Q1 were substantially the same as $Ca_4P_2O_9$.
Measurement of Specific Surface Area The specific surface area was measured by using the Macsorb HM-1220, available from Mountech Co., Ltd., in the condition of a degassing temperature of 230° C. and degassing time for 35 minutes. The measurement results for the fluorescent materials P1 to P5 and Q1 and Q2 obtained in Examples 1 to 5 and Comparative Examples 1 and 2 are shown in Table 1.
Measurement of Particle Size Distribution The particle size distribution was measured by a laser diffraction particle size analyzer (MT3000, available from Nikkiso Co., Ltd.), and a volume-based particle size distribution curve (also referred to as "particle diameter distribution") was obtained. At this time, the measurement was performed by mixing ion exchange water and a sample in a manner that the diffraction volume (DV) is from 0.01 to 0.2. The particle diameter value when the integration value in the volume-based particle size distribution curve was 50% was used as the average particle diameter D50 (μm). Similarly, the particle diameter value when the integration value was 10% was used as D10 (μm), and the particle diameter value when the integration value was 90% was used as D90 (μm). D90/D50 is a value obtained by dividing the value of D90 described above by the value of D50 described above. The measurement results for the fluorescent materials P1 to P5 and Q1 and Q2 obtained in Examples 1 to 5 and Comparative Examples 1 and 2 are shown in Table 1.

Furthermore, in the measurement results of the particle diameter distribution, the proportions of the particles having a particle diameter of 30 μm or greater and the particles having a particle diameter of 0.5 μm or less are also shown in Table 1.

TABLE 1

|  | P1 | P2 | P3 | P4 | P5 |
|---|---|---|---|---|---|
| Luminance Y | 2.6 | 2.8 | 2.9 | 2.4 | 2.5 |
| Chromaticity x | 0.1833 | 0.1780 | 0.1850 | 0.1748 | 0.1858 |
| Chromaticity y | 0.2170 | 0.1997 | 0.2178 | 0.1995 | 0.2334 |
| Specific surface area ($m^2/g$) | 5.2 | 2.8 | 1.4 | 5.1 | 5.4 |
| Particle size D10 (μm) | 2.5 | 4.0 | 2.0 | 2.8 | 2.3 |
| Particle size D50 (μm) | 5.1 | 6.8 | 4.5 | 5.3 | 4.9 |
| Particle size D90 (μm) | 8.1 | 10.6 | 7.1 | 8.7 | 7.9 |
| D90/D50 | 1.6 | 1.6 | 1.6 | 1.6 | 1.6 |
| Proportion of particles of 30 μm or greater (vol. %) | 0 | 0 | 0 | 0 | 0 |
| Proportion of particles of 0.5 μm or less (vol. %) | 0 | 0 | 0.16 | 0 | 0 |
| Dominant wavelength of light emission (nm) | 466 | 459 | 462 | 456 | 467 |
| Relative light emission intensity | 100 | 119 | 111 | 98 | 92 |

|  | Q1 | Q2 |
|---|---|---|
| Luminance Y | 7.4 | 0 |
| Chromaticity x | 0.1777 | — |
| Chromaticity y | 0.2133 | — |
| Specific surface area ($m^2/g$) | 0.12 | 10.9 |
| Particle size D10 (μm) | 40.7 | 0.48 |
| Particle size D50 (μm) | 110.5 | 0.72 |
| Particle size D90 (μm) | 197.2 | 1.49 |
| D90/D50 | 1.6 | 2.1 |
| Proportion of particles of 30 μm or greater (vol. %) | 99 | 0 |
| Proportion of particles of 0.5 μm or less (vol. %) | 0 | 17 |
| Dominant wavelength of light emission (nm) | 465 | — |
| Relative light emission intensity | 294 | 0 |

By applying the values of the chromaticity x and the chromaticity y of Table 1 into the chromaticity diagram, it was found that all of P1 to P5 emitted blue light. The luminance Y was also high, which was 1 or greater. From the excitation spectra of FIG. 6, it was found that the excitation occurred by visible light as well as by ultraviolet light. In particular, it was found that the excitation band spread to a visible light region of 400 nm or greater.

TABLE 2

|  | P1 | P2 | P3 |
|---|---|---|---|
| Luminance Y | 1.0 | 1.1 | 1.3 |
| Chromaticity x | 0.2208 | 0.2191 | 0.2156 |
| Chromaticity y | 0.3448 | 0.3401 | 0.3348 |
| Dominant wavelength of light emission (nm) | 495 | 495 | 492 |
| Relative light emission intensity | 28 | 38 | 33 |

By applying the values of the chromaticity x and the chromaticity y of Table 2 into the chromaticity diagram, it was found that all of P1 to P3 emitted blue/green light. The luminance Y was 1 or greater.

Evaluation Example 2 (Sensory Evaluation)

Sensory evaluation was performed for the texture of the powder and for light emission when the light of 365 nm was irradiated, by applying the fluorescent materials P1, Q1, and Q2 obtained in Example 1 and Comparative Examples 1 and 2 on skins of 10 members of a panel. The evaluation results of the texture are shown in Table 3.

TABLE 3

|  | P1 | Q1 | Q2 |
|---|---|---|---|
| Number of people who thought texture was excellent | 10 | 0 | 8 |
| Number of people who thought texture was poor | 0 | 10 | 2 |
| Number of people who observed blue light emission | 9 | 10 | 0 |
| Number of people who did not observe blue light emission | 1 | 0 | 10 |

Evaluation Example 3 (Sedimentation Velocity of Fluorescent Material Particle)

Using each of the fluorescent materials P1, Q1, and Q2 obtained in Example 1 and Comparative Examples 1 and 2, 2 g of the fluorescent material particle was dispersed in 40 mL of 0.025 wt. % of sodium hexametaphosphate aqueous solution and subjected to irradiation of the ultrasonic wave having a frequency of 20 kHz and an output of 90 W by using an ultrasonic homogenizer for 2 minutes. The obtained slurry was charged in a sedimentation column having an inner diameter of 2.5 cm and a capacity of 100 mL and left standing still for 1 minute, and the sedimentation velocity of the fluorescent material particles was calculated from the sedimentation height (height of the entire slurry−height of the precipitated cake) relative to the sedimentation time. The results are shown in Table 4.

TABLE 4

|  | P1 | Q1 | Q2 |
|---|---|---|---|
| Sedimentation velocity | 4 cm/min | 7 cm/min | 0.5 cm/min |

Evaluation Example 4 (Evaluation as Cosmetic)

Powder foundations F1 to F3 were prepared by using the fluorescent materials P1 to P3 obtained in Examples 1 to 3 according to the formulation shown in Table 5 below. Furthermore, a powder foundation F4 containing no fluorescent material particles of the present invention was prepared according to the formulation shown in Formulation Table 6 below. Note that the raw materials used in the foundation below are as shown in "Grade" of the table, and the raw materials except P1 to P3 are all in cosmetic grade.

TABLE 5

| Raw material | wt. % | Grade |
|---|---|---|
| Mica | 24.30 | Y-2300X (Yamaguchi Mica Co., Ltd.) |
| Sericite | 29.16 | FSE (Sanshin Koukou K.K.) |
| Plate-like barium sulfate | 11.70 | Plate-like barium sulfate-H (Sakai Chemical Industry Co., Ltd.) |
| Spherical silicone | 6.30 | KSP-105 (Shin-Etsu Chemical Co., Ltd.) |
| Titanium oxide | 7.20 | R-3LD (Sakai Chemical Industry Co., Ltd.) |
| Iron oxide (yellow) | 1.08 | Yellow iron oxide (Pinoa Co., Ltd.) |
| Iron oxide (red) | 0.36 | Red iron oxide (Pinoa Co., Ltd.) |
| Metallic soap | 0.90 | JPM-100 (Sakai Chemical Industry Co., Ltd.) |
| Oil | 9.00 | KF96 (Shin-Etsu Chemical Co., Ltd.) |
| P1, P2, or P3 | 10.00 |  |
| Total | 100 |  |

TABLE 6

| Raw material | wt. % | Grade |
|---|---|---|
| Mica | 27.00 | Y-2300X (Yamaguchi Mica Co., Ltd.) |
| Sericite | 32.40 | FSE (Sanshin Koukou K.K.) |
| Plate-like barium sulfate | 13.00 | Plate-like barium sulfate-H (Sakai Chemical Industry Co., Ltd.) |
| Spherical silicone | 7.00 | KSP-105 (Shin-Etsu Chemical Co., Ltd.) |
| Titanium oxide | 8.00 | R-3LD (Sakai Chemical Industry Co., Ltd.) |
| Iron oxide (yellow) | 1.20 | Yellow iron oxide (Pinoa Co., Ltd.) |
| Iron oxide (red) | 0.40 | Red iron oxide (Pinoa Co., Ltd.) |
| Metallic soap | 1.00 | JPM-100 (Sakai Chemical Industry Co., Ltd.) |
| Oil | 10.00 | KF96 (Shin-Etsu Chemical Co., Ltd.) |
| Total | 100 |  |

Each raw material was weighed in such a proportion, and agitation and mixing were performed for 1 minute and 30 seconds by using a coffee mill. In a mold having a diameter of 20 mm, 0.8 g of the obtained powdery mixture was weighed and placed. Then, a pressure of 200 kgf/cm$^2$ was applied by using a pressing machine for 30 seconds to obtain each of the powder foundations F1 to F4.

The powder foundations F1 to F4 were applied by 10 members of a panel without notifying them the identification numbers, and the beauty of the skin under irradiation of black light of 365 nm was tested. The results of the observation of beauty of skin, evaluated in the scale of one to five, are shown in Table 7. Note that the evaluation criteria are as shown below.

5: 8 or more or all of the members observed beauty

4: from 5 to 7 members observed beauty

3: from 2 to 4 members observed beauty

2: one member observed beauty

1: none of the members observed beauty

TABLE 7

|  | F1 | F2 | F3 | F4 |
|---|---|---|---|---|
| Observation of beauty | 4 | 5 | 4 | 2 |

The powder foundations F1 to F4 were applied by 10 members of a panel without notifying them the identification numbers, and the beauty of the skin under natural light was tested outdoor. The results of the observation of beauty of skin, evaluated in the scale of one to five, are shown in Table 8.

TABLE 8

|  | F1 | F2 | F3 | F4 |
|---|---|---|---|---|
| Observation of beauty | 4 | 4 | 4 | 1 |

The powder foundations F1 to F4 were applied by 10 members of a panel without notifying them the identification numbers, and the beauty of the skin under irradiation of fluorescent lamp was tested indoor. The results of the observation of beauty of skin, evaluated in the scale of one to five, are shown in Table 9.

TABLE 9

|  | F1 | F2 | F3 | F4 |
|---|---|---|---|---|
| Observation of beauty | 2 | 3 | 3 | 1 |

When the fluorescent material for cosmetics of an embodiment of the present invention is blended into a cosmetic, the beauty of skin can be observed under natural light outdoor and under fluorescent lamp indoor, and excellent cosmetic appearance can be achieved. In particular, white translucent finish can be achieved by correcting the yellowish color of the skin. From these results, it was found that the fluorescent material of an embodiment of the present invention can enhance optical functions.

Furthermore, P1 to P5 also exhibit excellent texture.

INDUSTRIAL APPLICABILITY

Since the fluorescent material for cosmetics of an embodiment of the present invention achieves excellent effects such as achieving excellent texture, imparting translucency to skin, and correcting the color so that the appearance of the skin color becomes beautiful, the fluorescent material can be suitably used in makeup cosmetics, such as foundations, makeup bases, and eye shadows; sunscreen agents; and the like.

In particular, because blue light is emitted by absorbing ultraviolet light of 365 nm contained in natural light (sunlight), the cosmetic of an embodiment of the present invention is effective under natural light and black light irradiation. Furthermore, the cosmetic can be a cosmetic that emits light by an excitation light in the visible light region and thus is effective even indoor or even in the case where flashlight or strobe are used to take a photograph.

The invention claimed is:

1. A fluorescent material for a cosmetic, the fluorescent material being a composite oxide containing Ce in a compound represented by general formula $Ca_aP_bO_c$, having an average particle diameter of from 1 to 10 μm, and
containing from 20 to 10000 ppm of potassium relative to a weight of the fluorescent material for a cosmetic,
wherein a molar ratio of Ce to phosphorous in the compound is 0.0005 to 0.05, and
$3.2 \leq a \leq 5.0$, $b=2$, and $c=a+5$.

2. A cosmetic, comprising:
the fluorescent material for a cosmetic according to claim 1; and
a cosmetic carrier,
wherein the cosmetic is selected from the group consisting of foundation, makeup base, eyeshadow, blush, mascara, lipstick, and sunscreen.

3. The cosmetic of claim 2, wherein the cosmetic contains 0.1 to 90 wt. % of the fluorescent material.

* * * * *